(12) United States Patent
Fields et al.

(10) Patent No.: US 6,539,252 B1
(45) Date of Patent: *Mar. 25, 2003

(54) METHOD AND APPARATUS FOR THE TREATMENT OF BLOOD BORNE PATHOGENS SUCH AS IMMUNODEFICIENCY VIRUS

(75) Inventors: Charles Bruce Fields, Pittsburg, CA (US); Phillip F. Burris, P.O. Box 221, Lafayette, CA (US) 94549

(73) Assignee: Phillip F. Burris, San Diego, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/491,782

(22) Filed: Jan. 26, 2000

Related U.S. Application Data

(62) Division of application No. 08/708,083, filed on Aug. 30, 1996, now Pat. No. 6,066,489.

(51) Int. Cl.⁷ .............................. A61N 1/30; A61M 5/00; A61M 31/00
(52) U.S. Cl. ..................... 604/21; 604/508; 604/264
(58) Field of Search ........................... 604/20, 21, 27, 604/28, 500, 508, 510, 264; 607/115, 122

(56) References Cited

U.S. PATENT DOCUMENTS

| | | | | |
|---|---|---|---|---|
| 873,021 A | * 12/1907 | Cool | ........................ | 604/21 |
| 3,878,564 A | 4/1975 | Yao et al. | ........................ | 3/1 |
| 3,964,477 A | * 6/1976 | Ellis et al. | | |
| 4,046,151 A | * 9/1977 | Rose | ........................ | 128/404 |
| 4,411,648 A | * 10/1983 | Davis et al. | ................... | 604/21 |
| 4,464,166 A | 8/1984 | Edelson | ........................ | 604/6 |
| 4,473,449 A | 9/1984 | Michaels et al. | ........... | 204/101 |
| 4,528,178 A | 7/1985 | Babb | ........................ | 424/7.1 |
| 4,605,394 A | 8/1986 | Skurkovich | ..................... | 604/4 |
| 5,043,073 A | 8/1991 | Brunner et al. | ............. | 210/646 |
| 5,091,152 A | 2/1992 | Thomas, Sr. | .................. | 422/23 |
| 5,133,932 A | 7/1992 | Gunn et al. | .................... | 422/24 |
| 5,139,684 A | 8/1992 | Kaali et al. | .................... | 21/748 |
| 5,185,086 A | 2/1993 | Kaali et al. | ................. | 210/748 |
| 5,188,738 A | 2/1993 | Kaali et al. | ................. | 210/748 |
| 5,322,520 A | * 6/1994 | Milder | ........................ | 604/265 |
| 5,328,451 A | * 7/1994 | Davis et al. | | |
| 5,409,467 A | * 4/1995 | Raad et al. | | |
| 5,669,874 A | * 9/1997 | Feiring | ........................ | 604/21 |
| 5,683,916 A | 11/1997 | Goffe et al. | ................. | 436/535 |
| 5,755,685 A | * 5/1998 | Andersen | ..................... | 604/53 |
| 5,759,489 A | 6/1998 | Miura et al. | .................. | 422/28 |
| 5,776,091 A | 7/1998 | Brugger et al. | ................ | 604/4 |
| 5,980,954 A | 11/1999 | Bolton | ........................ | 424/613 |
| 6,027,469 A | 2/2000 | Johnson | ........................ | 604/4 |
| 6,027,688 A | 2/2000 | Wainwright | .................. | 422/28 |
| 6,066,489 A | * 5/2000 | Fields et al. | ................. | 435/236 |

FOREIGN PATENT DOCUMENTS

GB          2189677 A    * 11/1987

* cited by examiner

Primary Examiner—Michael J. Hayes
(74) Attorney, Agent, or Firm—Charles C. Logan, II

(57) ABSTRACT

A method and apparatus for destroying blood borne pathogens is disclosed which utilizes a low intensity direct current to generate positive particles from various metals which destroy viral pathogens. A first electrode comprised of a metal such as silver is inserted into a patient's venous system. Then, a second electrode is placed on the patient's exterior in the vicinity of the first electrode. A low intensity direct current is applied to the first metal electrode which releases silver cations to be bonded to the virus, resulting in the denaturing of the virus. The first electrode is placed in the venous system of the infected patient via a catheter.

23 Claims, 7 Drawing Sheets

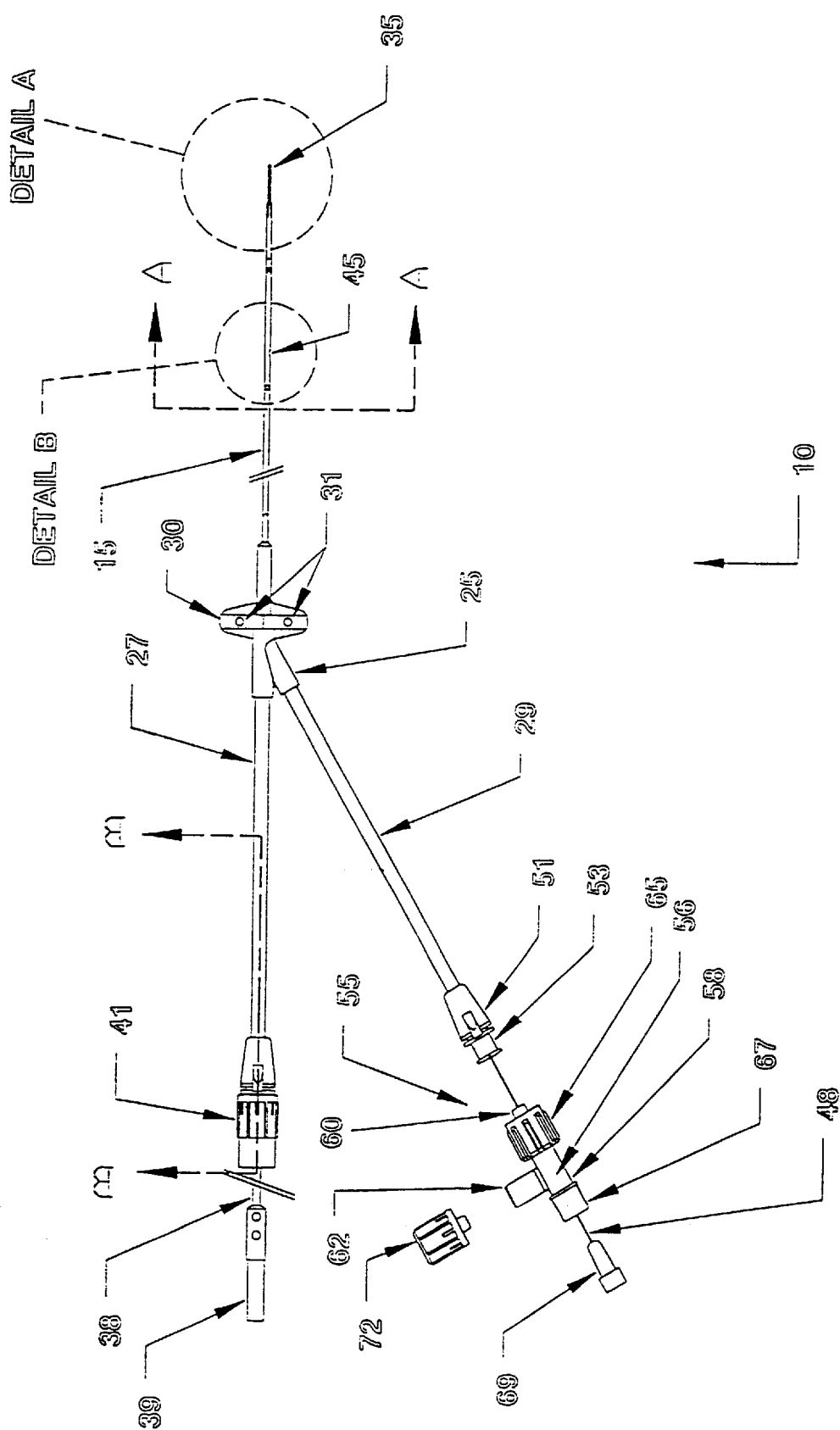

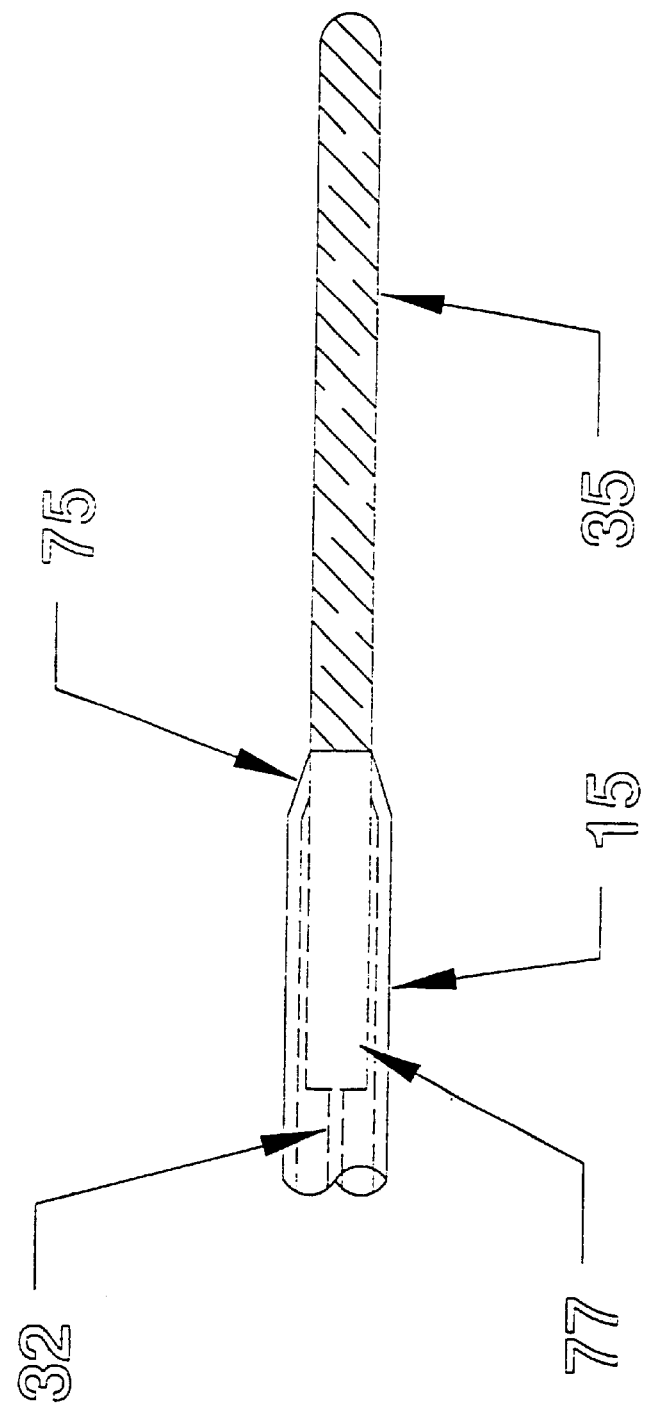

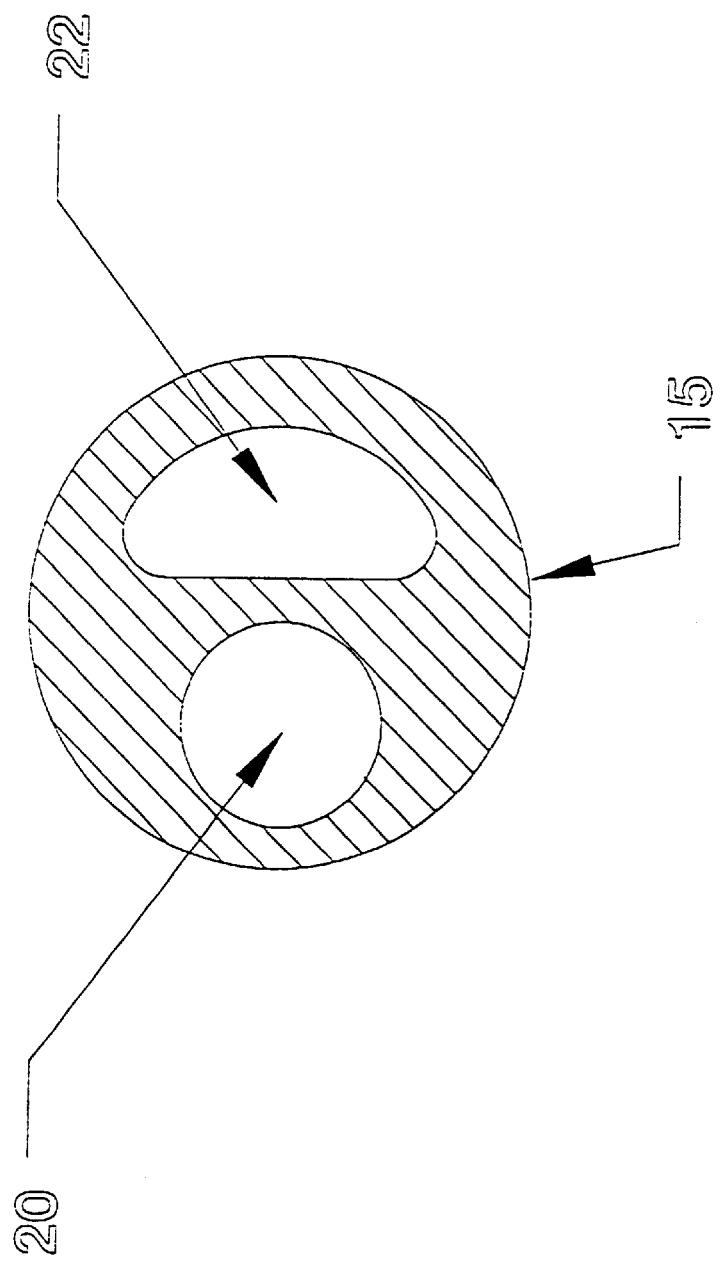

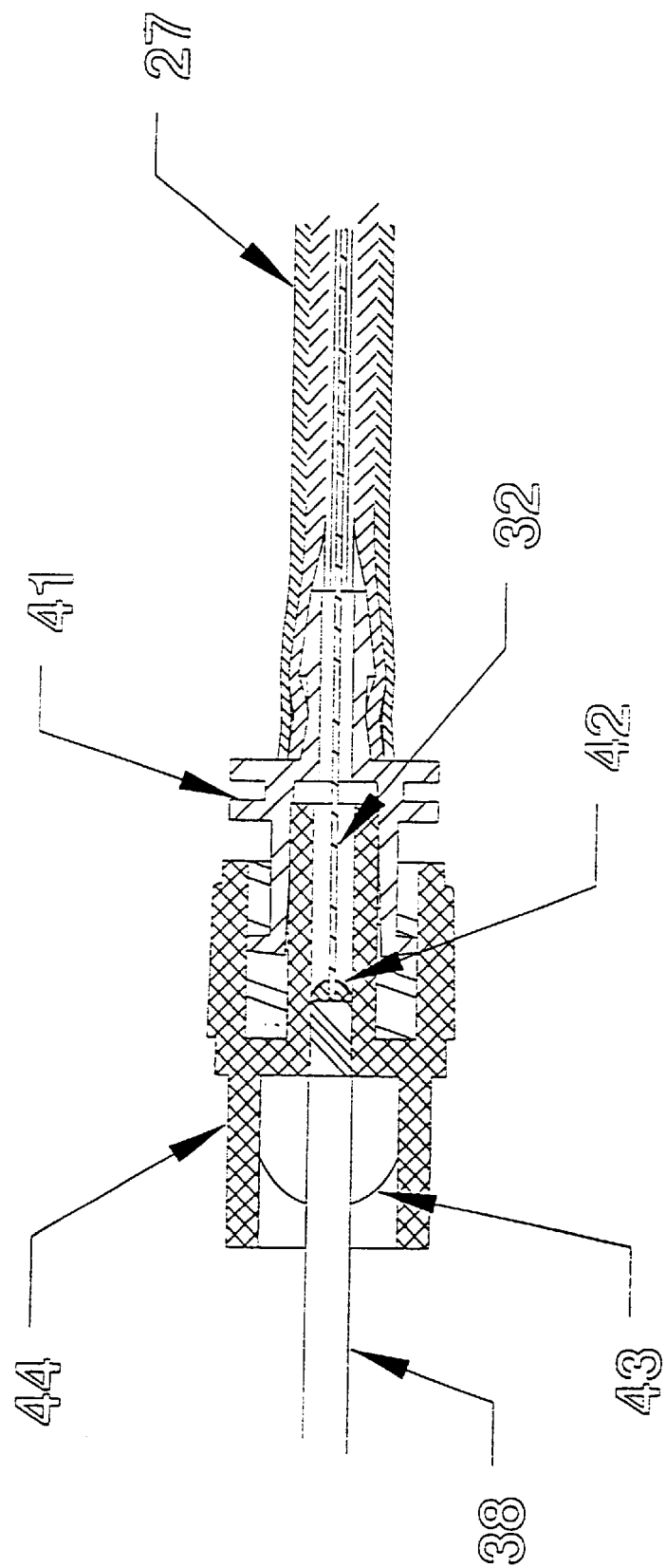

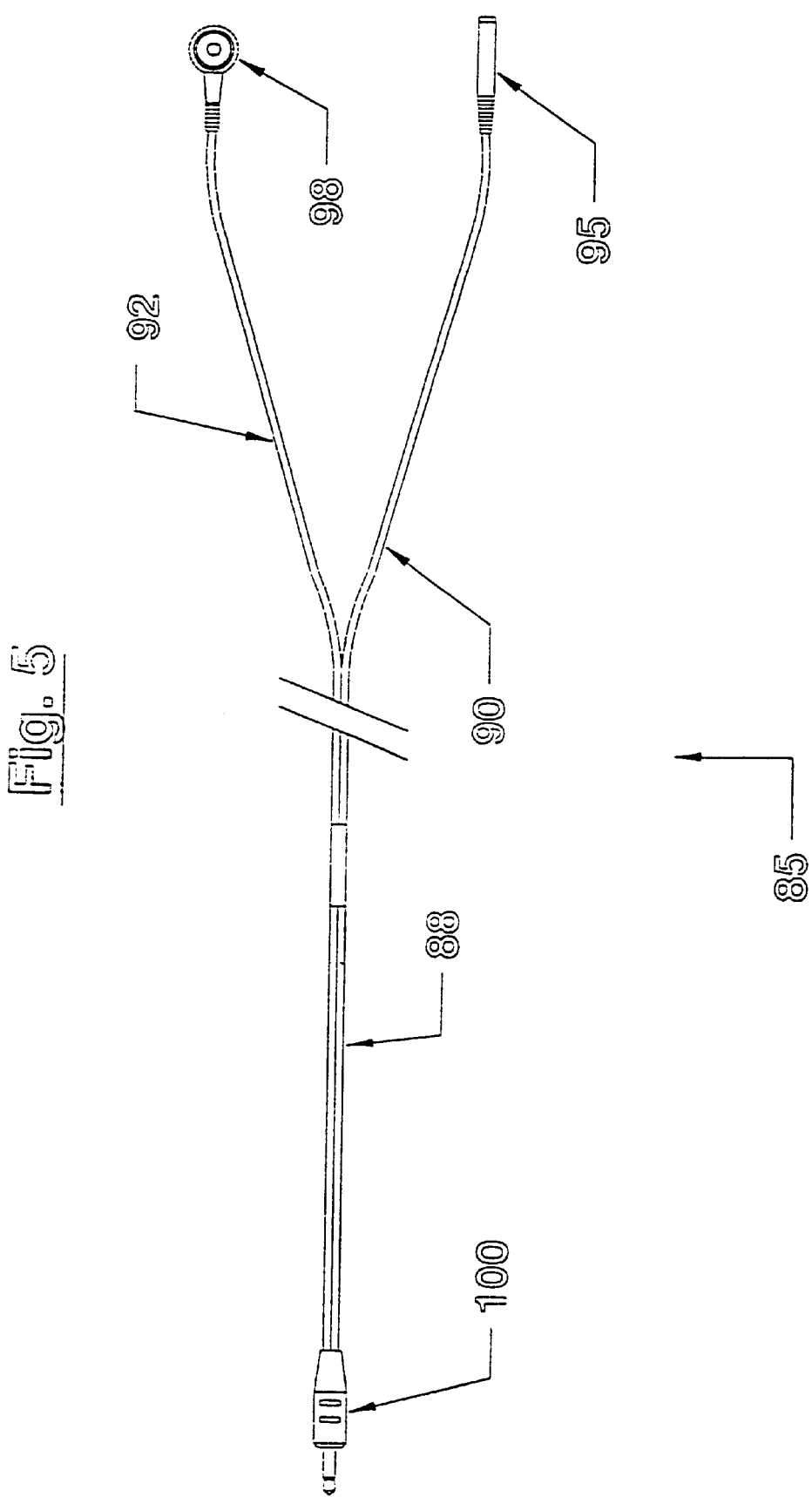

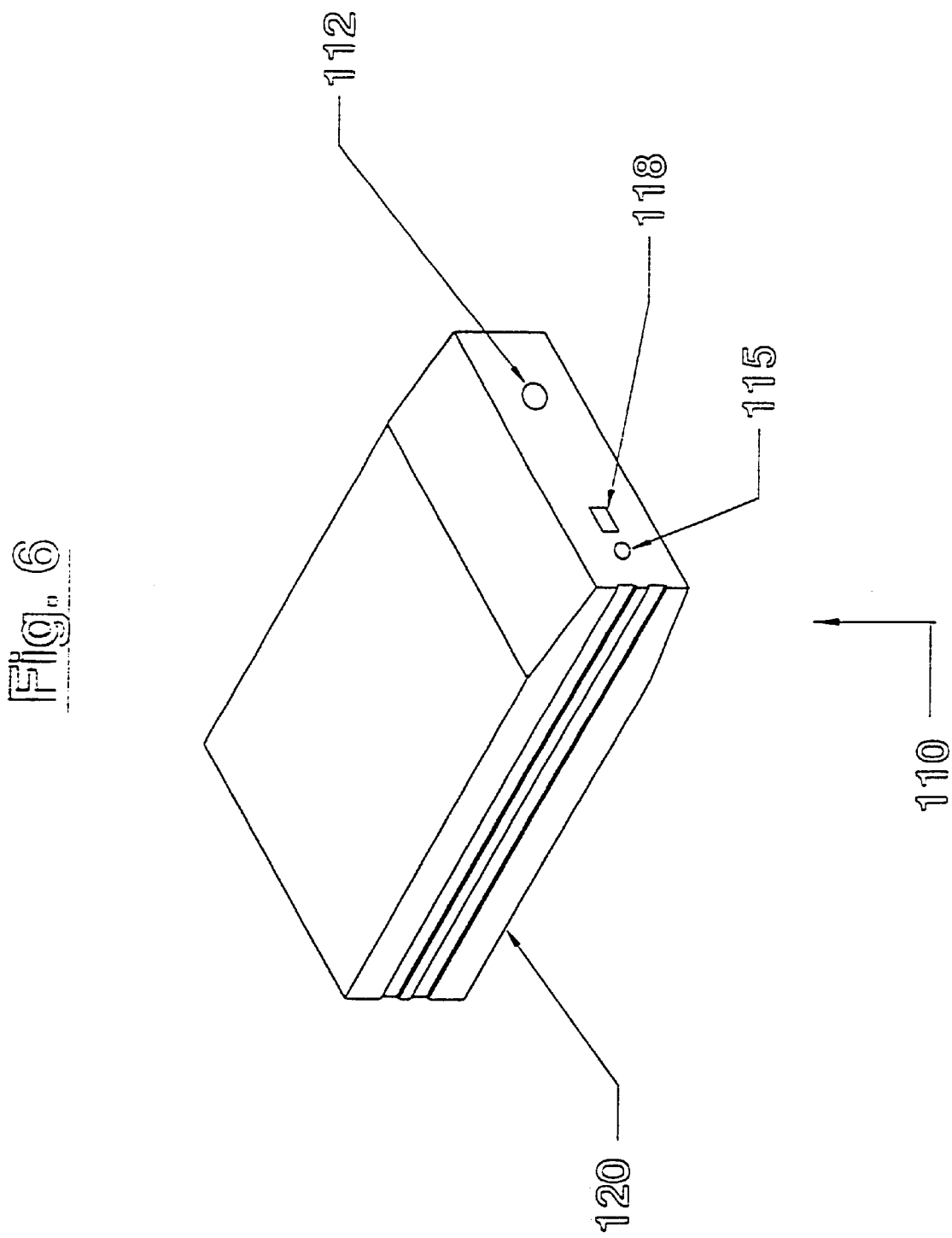

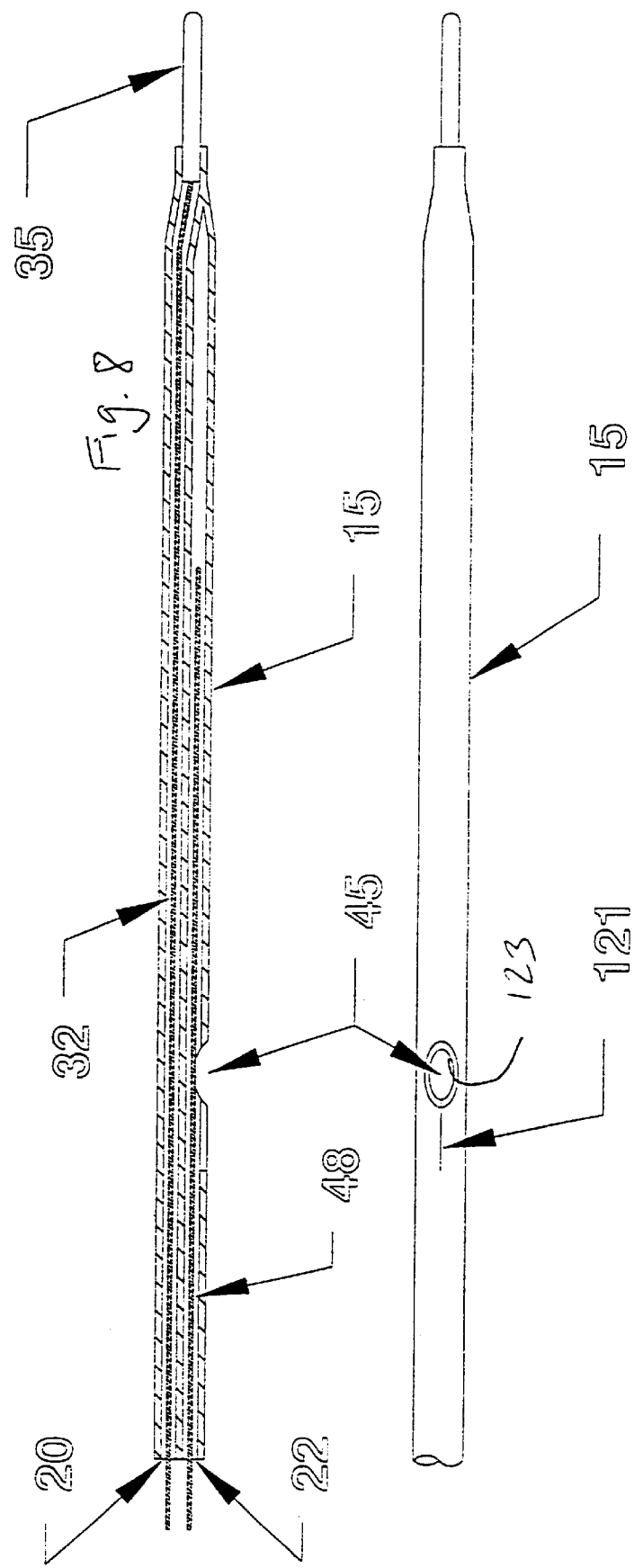

METHOD AND APPARATUS FOR THE TREATMENT OF BLOOD BORNE PATHOGENS SUCH AS IMMUNODEFICIENCY VIRUS

This is a division of application Ser. No. 08/708,083, filed Aug. 30, 1996, now U.S. Pat. No. 6,066,489.

FIELD OF THE INVENTION

This invention pertains to treatment of blood borne viral infections and more particularly concerns antiviral apparatus and methods.

BACKGROUND OF THE INVENTION

Blood borne viral infections are extremely difficult to treat or cure once a patient is infected with the virus. Blood borne viruses can completely inundate the patient (i.e., the "host") and defeat the patient's immune system, which almost certainly leads to death of the patient. Examples of viral infections affecting humans include polio, measles, chicken pox, small pox, mumps, Ebola, the common cold and the human immunodeficiency virus ("HIV"). In addition, animals are affected by other viral infections. For example, cattle can be infected by foot-and-mouth disease, dogs can be infected by distemper, cats can be infected by panleukopenia and feline immunodeficiency virus, and hogs can be infected by cholera.

The HIV virus has become a leading cause of death among humans. The prior art has not provided an effective antiviral agent which can effectively kill the HIV virus, thereby leading to either a cure or an effective treatment for infected patients.

The mechanisms of viral infections and specifically the HIV virus will now be discussed so as to provide background into how the present invention acts to kill viruses that have infected a patient. A virus is not an independent living organism. Outside of living cells, for example in body fluids, some viruses can remain dormant. They do not reproduce, metabolize, grow or assimilate food. For a virus to live and reproduce, it needs a host cell. Thus, until a virus finds a host cell, it it may remain dormant in body fluids. During this dormancy period, the virus may come in contact with a suitable host.

Viruses have many different shapes and sizes. For example, the individual virus or virions can be spherical, rod-shaped, or can have a many headed configuration. Virions range in size from approximately 0.02 microns to approximately 0.25 microns. The smallest living bacterium is approximately 0.4 microns. Virions are generally comprised of a viral core which is made up of nucleic acids which carry the viral genes and a capsis of fatty materials and proteins which surrounds the core. In some cases, viral proteins are associated with the nucleic acid in the viral core. This capsis may be surrounded by an additional lipoprotein envelope. The virus attacks a cell by causing at least its nucleic acid to enter the cell. The virus then takes over the cell's metabolic machinery and uses it to make many of copies of itself, thus producing many new virions. In the case of the HIV virus, the virions are released from the cell by lysing (i.e., the cell bursts), which destroys the cell. Many of the virions, however, are able to go on to infect other cells, which are eventually killed.

Humans and other animals have developed natural defenses to viruses. One of the body's first reactions to infection by a virus is a fever. Fever is often the only response necessary since elevated temperatures can deactivate many viruses. Other viruses cause cells to secrete the protein interferon. Interferon can inhibit the production of virions in uninfected cells. Another reaction to infection by a virus is the production of antibodies and activation of other parts of the body's immune system, which can inactivate the virus. Different viruses result in the production of different antibodies.

Part of the immune response of humans and other animals to viral infection is the production of T-lymphocytes and B-lymphocytes. T-lymphocytes and B-lymphocytes are classes of white blood cells that fight infection in a manner specific to the infecting agent. "B-cells" produce antibodies while "T-cells" have receptors on their surface that mate with the antigen of an invading agent. This mating prevents the invader from infecting other cells until that invading agent can be removed from the bloodstream by the kidneys. More than ten million different T-cell receptor patterns are known to exist. Once a specific T-cell has been produced to fight a specific agent, that T-cell continues to reproduce so that it is present at the time of the next infection by the agent it was created to fight. Approximately two-thousand T-cells can be produced by the body per second in a healthy individual.

The HIV virus is extremely deadly because it attacks these T-cells, eventually producing so many virions that attack the T-cells that the body cannot make T-cells fast enough to replace those destroyed by the HIV virus. The specific T-cell targeted by the HIV virus is the T4 helper lymphocyte. T4 cells are extremely important to the immune defense system of a human. T4 cells control the body processes which produce immune responses to infections. If a T4 cell determines that a response is necessary, it instructs the body's immune system to release T8 cytotoxic lymphocytes and antibodies.

When an HIV virion finds a T4 cell, it is believed that it attempts to penetrate the cell wall to gain access to the T4 cell's nucleus. Many believe that when the HIV virion contacts a T4 cell, the glycoproteins Gp120 and Gp41 on the exterior of the HIV virion attach the virion to CD4 proteins protruding from the T4 cell's surface. After attachment, it is thought that the HIV virus fuses with the T4 cell and injects capsid protein P24 with the genomic ribonucleic acid ("RNA") of HIV and reverse transcriptase, RNaseH, and integrase into the cell. After the HIV virus is injected into the cell, the reverse transcriptase, RNaseH, and integrase manufacture HIV deoxyribonucleic acid ("DNA") out of the genomic RNA. After the HIV DNA is manufactured within the cell, the HIV DNA enters the cell's nucleus and splices itself into one of that cell's chromosomes. At this point, the T4 cell is infected with the HIV virus.

Once the T4 cell is infected with the HIV virus, the T4 cell begins to reproduce copies, i.e., virions, of the HIV virus. One infected T4 cell can produce approximately three hundred thousand to one million copies of the HIV virus per infected T4 cell. Eventually, the infected T4 cell lyses, which destroys the cell. The copies of the infecting HIV virus released from the destroyed T4 cell go on, however, to infect other T4 cells. Since an infected T4 cell produces copies of the HIV virus faster than humans can produce T4 cells, eventually the immune system of the infected person is overrun and is unable to fight off infection. This is because there are too few T4 cells left to create an immune response to invading agents. It is these infections which eventually lead to the death of a patient from the HIV virus. Furthermore, copies of the HIV virus are created faster than the antibody the body creates to fight it. Since the T4 cells are destroyed faster than they can be reproduced, the body will never be able to create enough HIV antibody to fight the virus.

The prior art teaches that infection by many viruses can be prevented by vaccination. Vaccination involves injecting an uninfected patient with a weakened or denatured virus. In response to the weakened or denatured virus, the body will create antibodies specific to that virus. With respect to the HIV virus, however, there is no known vaccine. Further, because the HIV virus mutates so rapidly, a vaccine may not be possible. The prior art does teach several drug therapies for a person infected with the HIV virus. Prior art drug therapies include Azidothymidine, known as AZT, Dideooxyinosine, known as ddI, and Zalcitabine, known as ddc. Recently, a new class of drugs, for example Zidovudine, known as ZDV, and Saquinavir, ddc known as Invirase™, have been used for treating HIV infected patients. ZDV and Saquinavir are members of a class of drugs known as protease inhibitors. AZT tends to slow the HIV virus' reproduction cycle in humans. This lengthens the amount of time that it takes for the HIV virus to completely destroy the immune system. ddI has results similar to AZT and tends to be used if AZT is too toxic for a particular patient. ddc is generally used in combination with AZT to treat advanced HIV infection. AZT, ddI, and ddc are nucleotide analogues which make it difficult for the HIV virus to replicate by interfering with the reverse transcriptase. ZDV and other protease inhibitors are anti-retroviral agents that interfere with the replication machinery of HIV, resulting in non-infectious. Because the HIV virus mutates so rapidly, however, the virus within a patient eventually becomes immune to protease inhibitors.

Further, prior art methods have developed whereby the patient takes several different medications at the same time. These drug combinations have become known in the art as "cocktails." Cocktails of these drugs are proving somewhat effective at delaying the destruction of the immune system by the HIV virus. However, the HIV virus eventually does overrun the immune system in patients undergoing this therapy for the reasons discussed above. Furthermore, such treatment is extremely disruptive to the patient, as often the patient will be required to take thirty to forty pills at many different times during the day. The long-term results of these three-drug combinations are not yet known. Furthermore, the cost of the three-drug combination is extremely high and is therefore beyond the reach of many infected individuals. Finally, the three-drug treatments are not well tolerated by some patients.

Thus, there has been a long felt need for a treatment of subjects infected with blood-borne pathogens, such as the HIV virus, which destroys the pathogen.

SUMMARY OF THE INVENTION

Until the present invention, prior art treatments for subjects infected with viruses for which the body could not defeat with its own immune system only delayed death. For example, the prior art treatments discussed above for the HIV virus only lengthen the amount of time it takes for the HIV virus to destroy the immune system, which leads to death of the patient. The present invention provides a method and apparatus for destroying viruses such as the HIV virus, thereby eliminating the virus from the patient. The present invention utilizes a low intensity direct current to generate silver ions which destroy viral pathogens. The device operates in vivo via an exposed metal electrode in the bloodstream. A first electrode is inserted into a patient's venous system. This first electrode comprises silver. In a preferred embodiment, the first electrode comprises an alloy of silver, copper and platinum and traces of other metals. Then, a second electrode is placed on the patient's skin in the vicinity of the first electrode. Then, a low intensity direct current is applied to the first metal electrode. The low intensity direct current causes silver cations to be released from the electrode. The silver cations are attracted to the slight but distinct negative polarities of blood borne viruses. The bonding of the silver cation to the virus denatures the virus. The denatured virus is then removed from the bloodstream by the patient's kidneys.

In another embodiment of the present invention, a first low intensity direct current is applied to the first electrode for a first amount of time. Then, a second low intensity direct current is applied to the electrode for a second amount of time. The second amount of time is a significantly longer period of time.

A preferred embodiment of the present invention comprises a catheter having a first lumen, a proximal end and a distal end. An electrical conductor extends through the first lumen. The electrical conductor is in electrical communication with the first electrode, which extends out of the distal end of the catheter. A power supply is in electrical communication with the electrode and supplies the low intensity direct current.

The above and other preferred features of the invention, including various novel details of construction and combination of parts, will now be more particularly described with reference to the accompanying drawings and pointed out in the claims. It will be understood that the particular devices embodying the invention are shown by way of illustration only and not as limitations of the invention. As will be obvious to those skilled in the art, the principles and features of this invention may be employed in various and numerous embodiments without departing from the scope of the invention.

BRIEF DESCRIPTION OF THE DRAWINGS

Reference is made to the accompanying drawings in which are shown illustrative embodiments of aspects of the invention, from which novel features and advantages will be apparent FIG. 1 is a perspective view of an embodiment of the present invention.

FIG. 2 is an expanded side view of an electrode for use in a preferred embodiment of the present invention.

FIG. 3 is a view in section of a dual lumen catheter of an embodiment of the present invention.

FIG. 4 is a view in section of a connection point of a wire and a lead cable of an embodiment of the present invention.

FIG. 5 is a perspective view of a main power cable for a preferred embodiment of the present invention.

FIG. 6 is a perspective view of a power supply for use with preferred embodiments of the present invention.

FIG. 7 is a view of an exit port for one lumen of a dual lumen catheter of an embodiment of the present invention.

FIG. 8 is a view in section of the distal end of a catheter of the present invention.

DETAILED DESCRIPTION OF THE DRAWINGS

Ionic silver is useful in fighting bacterial infections and is widely used as a bacteriostatic agent. For example, electrically generated silver ions are effective on infectious bacteria in deep puncture wounds and on broken bones that have become infected. There are some indications that silver ions generated in small quantities (i.e., less than twenty parts per billion) in the blood stream are effective in destroying bacterial pathogens but remain totally nontoxic to mammalian cells. Silver ions are also toxic to eukaryotic microorganisms in levels as low as one to five parts per billion. The theories behind the effectiveness of silver ions are as follows.

All biological life forms have a negative charge. This phenomena can be photographed under certain conditions and is called an aura. Positive electrical energy is highly attracted to this negative polarization and is fatal to the life form when introduced directly, as in a human being standing near a tree in a lightening storm.

While this phenomena occurs in single cell and multi-cell animals, the individual cells comprising the animal, while having slightly positive or slightly negative polarities (it is these slightly positive and slightly negative polarities that allow magnetic resonance imaging systems to function) have an electromagnetic field surrounding the cell that is neutral. Therefore, because individual cells have polarity and are not polarized, positive cations are not attracted to individual cells.

As discussed, a virion is generally comprised of a core having nucleic acids and other protein-like substances and the virus' genomic RNA. Like the nucleus of a eukaryotic cell, the viral core has a slight but a distinct positive polarity and a slight but a distinct negative polarity. When the aggressive positive charges of the silver ions are placed in the vicinity of a virus, it is believed that the silver ions are attracted to the negative polarity of the core of the virus. This attraction leads to an ionic bond between the silver ion and the negative polarity of the virus' core. This bond leads to an exchange of a neutron between the silver ion and viral proteins. This leads to either the denaturization of the viral proteins or the breaking of the bonds in the virus' DNA, thereby killing the virus. Once the virus is killed, it is flushed from the blood by the patient's kidneys.

Silver salts such as silver chloride appear naturally in human blood serum at concentrations of approximately thirty to eighty parts per billion. Furthermore, silver is not reactive with body tissues. These characteristics, combined with the silver ion's efficacy in deactivating viruses make it ideal for treating patients with blood borne viral infections. However, one of ordinary skill in the art will recognize that other ions from the class of heavy metals will work well using the concepts of the present invention. An example of such heavy metals includes gold, zinc, copper, lead, and other metals capable of electrochemical reaction.

With reference to the drawings, presently preferred embodiments of the present invention will now be discussed. FIG. 1 shows a perspective view of an embodiment 10 of the present invention. The embodiment 10 of FIG. 1 comprises an elongated catheter 15. Catheter 15 is preferably made of a biocompatible polymer material such as silicone rubber, polyurethane, or the like and depending upon where on the patient it will be installed, can be a peripherally inserted central catheter. While a single lumen catheter is within the scope of the invention, a preferred embodiment of the present invention utilizes a dual lumen catheter 15 comprising first lumen 20 and a second lumen 22, as shown in FIG. 3. First lumen 20 is preferably circular in shape so as to accommodate an electrical conductor. Second lumen 22 preferably has a substantially "D" shape. Second lumen 22 is used to infuse medications or hydration fluids into the patient undergoing therapy while the embodiment 10 is installed. Second lumen 22 is particularly useful because patients infected with viruses are usually receiving many different medications, many of which could be dispensed through second lumen 22. Further, infected patients are often so dehydrated that their blood volume is too low to allow the present invention to operate effectively. The "D" shape of the second lumen 22, if used, maximizes the flow of fluids through this lumen 22.

Catheter 15 is fastened to bifurcation 25. Bifurcation 25 has a first leg 27 and a second leg 29 and wings 30 having suturing holes 31. First lumen 20 branches into first leg 27 and second lumen 22 branches into second leg 29. Bifurcation 25 can be either integral with first and second legs 27, 29 or securely fastened to first and second legs 27, 29. Disposed in first lumen 20 and passing through first leg 25 is a conductive wire 32, which is best seen with reference to FIGS. 2 and 4. Wire 32 can be constructed of any electrical conductor, but is preferably constructed of silver. In an alternative embodiment, catheter 15 can have wire 32 extruded therethrough, At the distal end of wire 32, anodal tip 35, i.e., an electrode, is installed thereon. Electrode 35 is fastened to wire 32 so that they are placed in electrical communication with each other. Preferred fastening techniques include soldering, welding, or brazing. After installation in a patient, anodal tip 35 will reside exposed in the bloodstream of the patient, as will be discussed below. At the proximal end of wire 32, a lead cable 38 fastened thereto. Lead cable 38 is fastened to wire 32 such that they are placed in electrical communication with each other. Preferred fastening techniques include soldering and welding. FIG. 4 shows the connection point 42 of the wire 32 and the lead cable 38. Lead cable 38 is fastened to wire 32 within connector 41. A seal 43 is placed within connector 41 (see FIG. 4). Seal 41 seals the first leg 25 and first lumen 20 from reflux of blood or other body fluids. At the proximal end of lead cable 38 is electrical connector 39. In a preferred embodiment, electrical connector 39 is a female electrical connector. However, other electrical connectors can be utilized without straying from the teachings of the present invention.

As discussed, second lumen 22 branches into second leg 29 at bifurcation 25 such that second leg 29 remains in fluid communication with lumen 22. Disposed on the side of catheter 15 is an exit port 45 (see FIG. 7). Exit port 45 is preferably one to two inches from the distal tip of catheter 15 so that any effluents released therefrom are not prematurely mixed into the ion field created by electrode 35. Lumen 22 initially may have a guidewire or stylet 48 slidably pre-inserted. Pre-inserted stylet 48 extends from lumen 22, through bifurcation 25 and leg 29. At the end of leg 29 is preassembled hub 51 which preferably has a Luer fitting 53 integral thereto. Stylet 48 extends out of leg 29 and passes through flushing assembly 55. Flushing assembly 55 comprises a three-way connector 56 having an inlet port 58, an outlet port 60, and a flushing port 62. Flushing assembly 55 has a Luer fitting 65 at the outlet port 60 which mates with the Luer fitting 53 on leg 29. A reclosable septum 67 is affixed at the inlet port 58. Septum 67 is preferably constructed of a resilient rubber material. The resilient nature of the rubber reclosable septum 67 is such that it makes a water tight seal around the stylet 48. The reclosable septum 67 provides a slight resistance to movement of the stylet 48. This resistance prevents the stylet 48 from being moved too quickly through the flushing assembly 55, leg 29 and catheter 15. This is advantageous since moving too quickly can cause patient discomfort and may result in puncturing the catheter 15 by the stylet 48. Puncturing the catheter 15 in an infected patient can be a serious problem since the user's ability to repair the damaged vein may be compromised by wire 32. Further, once stylet 48 is removed, the reclosable septum 67 forms a watertight barrier, which prevents the reflux of blood. The stylet 48 passes through lumen 22, leg 29, outlet port 60 inlet port 58 and reclosable septum 67. A stylet handle 69 may be placed at the end of the stylet 48 which emerges from the flushing assembly 55. Stylet handle 69 allows the installer to manipulate the stylet 48 during insertion so that the catheter can be maneuvered around obstructions in the patient's venous system.

The flushing port 62 of the flushing assembly 55 is used to add fluids such as flushing solutions to lumen 22 to aid in the installation of the catheter 15 into a patient. Flushing solutions also make removal of the stylet 48 after installation easier, as the fluids can lubricate the stylet 48. Flushing solutions are added to flushing assembly 55 by affixing a syringe (not shown) to flushing port 62. When a syringe is not affixed to flushing port 62, a cap 72 may be placed over the flushing port 62. A preferred flushing apparatus and method are disclosed in U.S. Pat. No. 5,357,961. U.S. Pat. No. 5,357,961 is assigned to the assignee of the present invention, and is incorporated herein by reference in its entirety.

FIG. 2 shows a detailed view of an embodiment of the electrode 35 used in the present invention. The electrode 35 is frictionally attached to the catheter 15 at the catheter's distal end 75 and preferably is one-half inch long and 0.03 inches in diameter. The security of the fit between the distal end 75 of catheter 15 and the electrode 35 is important as it is highly desirable to prevent fluids such as blood or other fluids from leaking around the electrode 35 and into lumen 20. Catheter 15 preferably tapers at its distal end 75 to allow for a smooth transition into electrode 35 (see also FIGS. 7 and 8). Approximately eighty percent of the electrode 35 is uninsulated and therefore exposed. That portion of the electrode 35 that resides within lumen 20 of catheter 15, along with wire 32, is preferably covered by insulation 77. Insulation 77 is preferably a biocompatible insulation material such as parylene. Other polymers like parylene can be used as an acceptable insulation material. In a preferred embodiment, the electrode 35 is an alloy comprised of 97.8 percent silver, 0.2 percent copper, and 2.0 percent platinum. While the silver component produces the ions most reactive with viruses, the copper and platinum of electrode 35 provide very important features. The platinum acts as a catalyst and aids in the release of the silver ions from the electrode 35. The platinum also helps to prevent oxides from building up on the electrode 35. The copper acts to control the release of silver ions from the electrodes. In particular, the copper causes the silver ions to be released in short bursts.

FIG. 3 shows a cross-sectional view of a dual lumen catheter 15. As discussed, the present invention contemplates the use of a single lumen catheter as well as the dual lumen catheter shown in FIG. 3. If a single lumen catheter is used, only lumen 20, which contains wire 32, will be present. If fluids or medications are infused into the patient's bloodstream, other means will be required. In addition, the present invention contemplates the use of catheters having more than two lumens, such as a triple lumen catheter.

FIG. 4 shows a cross sectional view of the electrical connection of wire 32 to lead cable 38 inside connector 41. Connector 41 fits snugly within first leg 27, as shown in FIG. 4. A Luer fitted cap 44 fits over connector 41.

FIG. 5 shows a main power cable 85 of an embodiment of the present invention. Power cable 85 is comprised of a main cable 88 and two separate branches 90 and 92. First branch 90 terminates at an electrical connector 95. Electrical connector 95 can be securely connected to electrical connector 39. In a preferred embodiment, electrical connector 95 is a male connector. Second branch 92 terminates an electrode pad 98. Electrode pad 98 can be an EKG pad. Main cable 88 terminates at another electrical connector 100. In a preferred embodiment, electrical connector 100 is a male electrical connector.

FIG. 6 shows a power supply 110 which is used to apply power to the electrode 35. Electrical connector 100 of power cable 85 fits securely within a jack 112 on power supply 110. In a preferred embodiment, jack 112 is a female electrical socket which can receive connector 100 from power cable 85. Also on power supply 110 is a display 115 which, when illuminated, indicates that the power supply 110 is supplying current to the electrode 35. A switch 118 is provided which allows the amount of current to be varied. In a preferred embodiment, switch 118 has two positions which provide two different levels of current to electrode 35. The amount of current supplied at the two different positions will be discussed below. Using the teachings of the present invention, however, it is possible that different types of switches may be provided so that more than two levels of current can be supplied to the patient. Further, in another preferred embodiment, the power supply 110 is able to automatically switch between the different levels of current that must be supplied to treat the virus which the patient is infected with. Power supply 110 is preferably housed in a sealed case 120 constructed of a material that can be sterilized with ethyleneoxide. Power supply 1 10 should be powered by a self-contained power source such as a battery which is capable of providing the power necessary for a substantial length of time, e.g., six-to-eight weeks. In a preferred embodiment, the power supply 110 is powered by a nine volt alkaline battery which is sealed within case 120. Preferably, provisions are made to allow the replacement of the battery should the need arise. In another embodiment, the power supply can be powered by a 1.5 volt alkaline battery.

FIGS. 7 and 8 show the distal end of catheter 15. FIG. 7 shows a preferred embodiment of exit port 45. Presently preferred exit port 45 comprises an axially oriented, oval-shaped opening 123 and an axially oriented slit 121 extending from an end of opening 123 toward bifurcation 25. Slit 121 is expandable from a closed position to an open position. Slit 121 opens by separating the top and bottom portions beginning at the opening 121. An embodiment of such a side port is found U.S. patent application Ser. No. 08/660,020, filed on Jun. 6, 1996, now U.S. Pat. No. 5,776,096. This application is incorporated herein by reference.

As will be discussed below, the power supply 110 supplies a low intensity direct current to the electrode 35. Because the electrode 35 releases silver cations, there is a chemical reaction that occurs on the surface of the electrode involving silver and oxygen that results in a nonconductive oxide on its surface. Over the treatment period, this oxide increases the surface resistance on the electrode 35. This increased resistance requires that the power supply 110 increase the voltage applied to the electrode 35 to produce the same number of silver ions throughout the treatment period. Thus, in a preferred embodiment, the power supply 110 adjusts its voltage to maintain the proper current level and hence voltage level. However, at 0.88 volts and higher, the oxide can be forced off of the electrode, which could cause blood clots, stroke and the like. Therefore, a preferred embodiment of the present invention has a voltage limit of 0.86 volts. If the power supply 110 is required to supply more than 0.86 volts, it will shut down. In a preferred embodiment, the power supply 110 has a display (not shown) which would inform the clinician or the patient that the power supply 110 has shut down. The display could also provide other pertinent information such as the level of current and voltage being supplied and the elapsed time of treatment. An audible warning can also be provided that is indicative of a possible malfunction. In the case where the power supply 110 shuts down because it exceeded 0.86 volts, the apparatus 10 can be removed and a new one can be installed in the manner described herein. The current supply capability of the electronics of power supply 110 will be discussed below.

In another preferred embodiment of the present invention, the power supply 110, cable 85 and apparatus are integral with each other.

The method of installation of the apparatus 10 of the present invention will now be discussed. One of ordinary skill in the art will recognize that many other installation procedures may be appropriate depending upon the patient and the preferences of the installer. Prior to installation, a proper location must be found on the patient for insertion of the catheter. Generally, a location on one of the arms of the patient is selected where venous introduction will be possible. Because patients infected by such blood borne viruses as HIV virus may have experienced severe weight loss, disease and other problems, the present invention can be installed through the veins or arteries in areas of the body other than the arm. For example, the apparatus 10 can be installed in the jugular vein of a patient.

As discussed, a stylet 48 is runs the length of lumen 22 of catheter 15. Stylet 48 makes installation of the apparatus 10 easier because it stiffens catheter 15, which makes pushing it through a patient's venous system easier. This is especially important in patients severely affected by viruses because they are often dehydrated. Dehydration makes passing catheters through the venous system difficult, as there is less blood volume. Stylet 48 preferably comprises a hydrophilically coated, twist-braided stylet. As discussed, handle 69 provides a larger surface which makes manipulating the stylet 48 easier. This can reduce the amount of time it takes to install the catheter. Shortened installation times are especially important with infected patients because during installation, blood can reflux from the patient, which can place the installer in danger of infection.

After the installation site is selected, it is prepared for apparatus 10 insertion. If desired, a small amount of flushing solution can be flushed through flushing port 62 and into leg 29 and lumen 22. Flushing prior to installation allows the user to check for patency. The user will know that the catheter 15 has been successfully flushed when drops of flushing solution begin to emerge from the exit port 45 of second lumen 22. After ensuring patency, the vein is punctured through the skin using a catheter introducer (not shown). Suitable introducers include the SAFE-T-PEEL® brand break-away introducer from HDC Corporation and any other over the needle type peel away introducer. After the introducer provides access to the patient's vein, the catheter 15 is threaded through the patient's venous system until the electrode 35 reaches his or her superior vena cava. As will be discussed below, the superior vena cava is the preferred location for the electrode 35.

While threading the catheter 15 through the patient, it may be necessary to flush the second lumen 22 of catheter 15 to aid in installation. When the second lumen is flushed during installation, the flushing solution will act to slightly move the tip of catheter 15, thereby allowing it to move past any venous obstruction. Flushing during installation can also remove any blood that may accumulate inside the second lumen 22. After the apparatus 10 is installed in the patient and the electrode 35 is placed within the superior vena cava, the stylet 48 should be removed from the second lumen 22. To remove the stylet 48, the stylet's 35 handle 69 is pulled. If any resistance is felt, the second lumen 22 can be flushed. As discussed above, the flushing solution lubricates the stylet 48, thereby making removal much easier. Once the electrode 35 is properly placed, apparatus 10 can be affixed to the patient via suturing holes 31.

Once the apparatus 10 is installed in the patient, the main cable 85 is installed. The electrode pad 98 is affixed to the exterior skin of the patient such that it is in close proximity to the electrode 35 installed within the patient. Then, connector 95 at the end of branch 90 of cable 85 in is connected to connector 39 on lead cable 38. Then, connector 100 on main cable 88 is connected to jack 112 on power supply 110. As discussed above, in another preferred embodiment, the power supply 110, cable 85 and apparatus 10 are integral with each other. Such an arrangement eliminates the need for the installer to make these connections. As it will be necessary for an apparatus of the present invention to remain installed in the patient for a long period of time, the apparatus 10, cable 85 and power supply 110 should be arranged on the patient so that the patient can remain comfortable and have the ability to move about.

The present invention operates by providing a low intensity direct current to electrode 35. By placing the electrode pad 98 on the surface of the patient in the vicinity of electrode 35, the low intensity direct current will cause the electrode 35 to act as an anode, thereby releasing metal ions into the bloodstream of the patient. These positively charged metal ions are attracted to the negative polarity of the virus, thereby destabilizing it, as discussed above. The superior vena cava of the patient is the preferred location for installation of electrode 35 because it is the largest blood vessel in the body. The use of such a large blood vessel is preferred because metal ions such as the preferred silver ion have a half life of approximately seven seconds. The device as will be seen below, creates an average output of four-hundred billion silver cations per second. With an average blood volume of four liters passing by the electrode 35 approximately twice per minute, the probability of a virus passing by the electrode 35 and being bonded to a metal ion increases when the volume of blood available to carry the virus is higher. Thus, placing the electrode 35 in the superior vena cava will increase the probability that metal ions generated by the apparatus 10 will bond to a virus in the bloodstream.

It is very important that the amount of metal ions entering the bloodstream from the apparatus 10 be controlled so that while large numbers of virus are killed, the patient is not harmed. The human body has naturally occurring silver ions as components of stable salts present in the bloodstream. These particular silver ions are present in human blood serum in concentrations of approximately thirty to eighty parts per billion as previous experiments have shown. However, these naturally occurring ions are associated with other negatively charged ions. Because of this, they are not attracted to the viruses present in the bloodstream and therefore cannot kill any viruses.

In the presently preferred method of administering metal ions to an infected patient, the patient is initially flooded with large amounts of metal ions for a relatively short period of time. The reason for this is that a patient infected with a pathogen such as the HIV virus may have two million or more copies of the virus per milliliter of blood. With the average human having approximately four-thousand milliliters of blood, an infected individual may have approximately eight billion copies of the virus that must be bonded to a silver ion. Since silver ions have a relatively short half-life (approximately seven seconds), a significantly larger number of silver ions must be produced than there are viruses because the probability of a silver ion bonding to virus is much lower than one-hundred percent However, the need for large numbers of silver ions must be balanced with the need to keep the silver content within levels safe for humans. Since humans can withstand only approximately thirty to eighty parts per billion of silver in the blood serum without resulting in a toxic reaction, it is important that the present invention not introduce more than this safe amount into the bloodstream.

To balance the need for large numbers of silver ions with the need to keep the amount of silver within safer ranges for humans, the power supply 110 supplies two and one-half microamps of current for twelve minutes at the beginning of treatment. This produces $1.56 \times 10(13)$ ions of silver per second. During the twelve minutes (i.e., seven-hundred twenty seconds) that the power supply 110 supplies two and one-half microamps of current, 0.0018 Coulombs enters the bloodstream (i.e., seven-hundred and twenty seconds multiplied by two and one-half microamps). Under Faraday's law, one mole of silver ions equals 96485 Coulombs. Further, one mole of silver ions weighs 107.87 grams. Thus, in the initial twelve minute operating period, nearly two micrograms (1.94 micrograms) of silver ions are introduced into the bloodstream. This is less than five parts per billion silver content in the blood serum, which is significantly below the level of harmful silver content within a human. Thus, during the initial twelve minute treatment using the concepts of the present invention, the silver content does not exceed toxic levels.

After the initial twelve minute operating period, the low intensity direct current provided by power supply 110 is reduced to one-hundred twenty five nanoamps. This causes the production of silver ions to be produced at a rate of seven-hundred seventy-four billion ions per second. Under a preferred embodiment of the present invention, this level of electric current is maintained for a period of seventy-one hours and forty-eight minutes. During this time (i.e., 258,480 seconds) that the power supply 110 supplies one-hundred twenty-five nanoamps of current, $3.2 \times 10(-4)$ Coulombs enters the bloodstream (i.e., 258,480 seconds multiplied by one-hundred twenty-five nanoamps). Under Faraday's law, one mole of silver ions equals 96485 Coulombs. Further, one mole of silver ions weighs 107.87 grams. Thus, during this entire period, only approximately 36.1 micrograms of silver ions are introduced into the bloodstream. Thus, in the entire seventy-two hour treatment, only 38.1 micrograms of silver have been introduced into the patient's bloodstream. This is less than nine parts per billion silver content in the blood serum for a seventy-two hour period, which is significantly below the range for harmful silver content within a human.

The present invention, in addition to providing a non-toxic level of silver ions into the bloodstream, does not exceed unsafe levels of current. Low intensity direct currents of two and one-half microamps and one-hundred twenty five nanoamps is far lower than the current levels provided by, for example cardiopacing devices. Thus, the small amounts of silver ions introduced into the patient's bloodstream coupled with the extremely low currents result in a treatment that, in addition to being highly effective, is also physiologically safe.

The concepts of the present invention have been tested on subjects and resulted in highly positive results. In a first example, the human patient had 2,165,823 copies of the HIV virus per milliliter of blood by the RNA PCR quantification test method. In addition, this patient's T4 cell (Helper) count was at 18. This particular subject was experiencing serious kidney malfunction prior to treatment. Twenty-four hours after treatment, this patient's viral load was reduced to 1,336,817 copies of the HIV virus per milliliter of blood while the T4 cell count was 11. Because of this patient's kidney malfunction, it was suspected that most of the viral copies detected during the RNA PCR quantization test had been denatured but had not yet been removed from the patient by the kidneys. Thus, one month after treatment, the viral load was measured again and found to be reduced to 621,215 copies of the HIV virus per milliliter of blood. After treatment, the patient immediately felt improved health, was able to eat solid food, and experienced a dramatic increase in quality of life.

A second human subject had a viral load of 1,814,466 copies of the HIV virus per milliliter of blood (RNA PCR quantification method) and a T4 cell count of 17. This patient was too dehydrated to place the electrode 35 into the superior vena cava. Thus, the electrode 35 was placed in the subclavian vein. This patient was subjected to twelve minutes of treatment at 2.5 microamps and then only forty-seven hours and forty-eight minutes of treatment at one-hundred twenty-five nanoamps. Forty-eight hours after treatment, the patient's viral load and T4 cell count were measured to be 394,972 copies of the HIV virus per milliliter of blood (RNA PCR quantization method) and 18, respectively. Once again, this patient immediately felt improved health and was able to eat solid food.

A third human subject had a viral load of 693,832 copies of the HIV virus per milliliter of blood (RNA PCR quantification method) and a T4 cell count of 5. This patient was also undergoing treatment with AZT. For this patient's treatment, the initial twelve minutes of treatment at 2.5 microamps was followed by seventy hours and eighteen minutes of treatment at one-hundred twenty-five nanoamps. Twenty-four hours after treatment, the patient's viral load and T4 cell count were measured to be 634 copies of the HIV virus per milliliter of blood (RNA PCR quantization method) and 6, respectively. Once again, this patient immediately felt improved health, was able to eat solid food, and experienced a dramatic increase in quality of life.

In a presently preferred method for practicing the invention, the low intensity direct current is maintained for a longer period of time than the seventy-two hour period discussed above. The reason for this is that it is currently believed that it takes approximately six weeks for an HIV virus that infects a cell to cause that cell to lyse (i.e., burst). Any viruses that infected a cell immediately prior to treatment with the methods of the present invention could avoid being denatured by a metal ion while reproducing in a T4 cell. Thus, for a six week period following treatment, T4 cells will lyse, causing new HIV virions to enter the bloodstream. These new HIV virions can eventually infect new cells. Because of this, while the patient's health may be improved in the short term, the HIV virus will once again work to destroy the immune system in the fashion discussed above. Thus, in a presently preferred embodiment, the patient receives an initial treatment of 2.5 microamps for twelve minutes. Then, the low intensity direct current is lowered to one-hundred twenty-five nanoamps for a period of six weeks by doing this, the invention can denature the HIV virions produced by lysing cells after treatment begins.

By doing so, virtually all of the HIV virions can be denatured, thereby resulting in a potential cure.

The methods of this invention have also been successfully tested on a different virus and a different host: namely, a cat infected with feline immunodeficiency virus ("FIV"). A seven year old male house cat weighing ten pounds and ten and three-quarter ounces had "heavy third eyelid", some hair loss, eleven bite marks along his back and rump, and a wound to the top of the ear, all indicative of acute disease. The cat was anesthetized with ketamine, a catheter was placed in the neck, and the negative electrode was placed on the underchest. Approximately four micrograms of silver was delivered in twenty-four minutes, followed by one-half a microgram of silver per hour for ninety minutes. The next morning the subject cat had returned to normal activity and appetite.

Thus, method and apparatus for the treatment of blood borne viral infections such as human immunodeficiency virus and feline immunodeficiency virus is disclosed. While embodiments and applications of this invention have been shown and described, it would be apparent to those skilled in the art that many more modifications are possible without departing from the inventive concepts herein. The invention, therefore is not to be restricted except in accordance with the scope of the appended claims. Furthermore, one skilled in the art will recognize that the present invention is useful for treating infections other than the HIV virus. For example, the teachings of the present invention would be effective at treating patients infected with such blood-borne pathogens as bacteria, fungi, Rickettsia, etcetera.

We claim:

1. An apparatus comprising:
   a catheter having a first lumen and a second lumen, a proximal end and a distal end;
   a bifurcation fitted at said proximal end of said catheter, said bifurcation having a first leg and a second leg, said first leg having a first connector attached thereto, said second leg having a second connector attached thereto;
   an electrode extending out of said distal end of said catheter for the in situ creation and release of cations from the electrode directly into the blood of a venous system of a patient,
   an electrical conductor extending through said first lumen and said first leg of said bifurcation, said electrical conductor being in electrical communication with said electrode;
   a lead cable electrically connected to said electrical conductor at said first connector;
   a main cable, said main cable comprising a first branch and a second branch, said first branch electrically connected to said lead cable, said second branch electrically connected to an electrode pad;
   an electrode pad disposed on the patient;
   a power supply, said power supply in electrical communication with said first branch of said main cable and said electrode pad, said power supply adapted to supply direct current to said electrode; and
   a catheter flushing apparatus connected to said second connector, said catheter flushing apparatus having a stylet extending from said catheter flushing apparatus, said second leg of said bifurcation and said second lumen of said catheter.

2. The apparatus of claim 1 wherein said electrode is comprised of silver.

3. The apparatus of claim 1 wherein said electrode is comprised of silver, platinum and copper.

4. The apparatus of claim 3 wherein said electrode is comprised of approximately 97.8 percent silver, 0.2 percent copper, and 2.0 percent platinum.

5. The apparatus of claim 1 wherein said catheter further comprises an side portal which allows fluids to exit said second lumen.

6. The apparatus of claim 1 wherein said second lumen has a D shape.

7. An apparatus comprising:
   (A) a catheter having a first lumen and a second lumen, a proximal end and a distal end;
   (B) a bifurcation fitted at said proximal end of said catheter, said bifurcation having a first leg and a second leg, said first leg having a first connector attached thereto, said second leg having a second connector attached thereto;
   (C) a first electrode extending out of said distal end of said catheter for the in situ creation and release of cations from the electrode directly into the blood from the circulatory system of a patient;
   (D) an electrical conductor extending through said first lumen and said first leg of said bifurcation, said electrical conductor being in electrical communication with said first electrode;
   (E) a lead cable electrically connected to said electrical conductor at said first connector;
   (F) a main cable, said main cable comprising a first branch and a second branch, said first branch electrically connected to said lead cable, said second branch electrically connected to a second electrode;
   (G) a second electrode;
   (H) a power supply, said power supply in electrical communication with said first branch of said main cable and said second electrode, said power supply adapted to supply direct current to said first electrode; and
   (I) a catheter flushing apparatus connected to said second connector, said catheter flushing apparatus having a stylet extending from said catheter flushing assembly apparatus, said second leg of said bifurcation and said second lumen of said catheter.

8. The apparatus of claim 7 wherein said first electrode is comprised of silver.

9. The apparatus of claim 7 wherein said first electrode is comprised of silver, platinum and copper.

10. The apparatus of claim 9 wherein said first electrode is comprised of approximately 97.8% silver, 0.2% copper, and 2.0% platinum.

11. The apparatus of claim 7 wherein said catheter further comprises a side portal which allows fluids to exit said second lumen.

12. The apparatus of claim 7 wherein said second lumen has a D shape.

13. An apparatus comprising:
   a catheter having a first lumen, a proximal end and a distal end;
   an electrical conductor extending through said first lumen;
   an electrode extending out of said distal end of said catheter for the in situ creation and release of cations from the electrode directly into the blood of a venous system of a patient, said electrode being solid and in electrical communication with said electrical conductor, said electrode defining a distal end configured and dimensioned for passage through the patient's skin and into the blood of the patient's venous system; said electrode is comprised of approximately 97.8 percent silver, 0.2 percent copper, and 2.0 percent platinum; and
   a power supply, said power supply in electrical communication with said electrode and with an electrode pad on the patient.

14. An apparatus comprising:
a catheter having a proximal end and a distal end;
an electrical conductor extending through said catheter;
an electrode extending out of said distal end of said catheter for the in situ creation and release of cations from the electrode directly into the blood of a venous system of a patient, said electrode defining a distal end configured and dimensioned for passage through the patient's skin and into the blood of the patient's venous system, said electrode being in electrical communication with said electrical conductor;
said electrode is comprised of approximately 97.8 percent silver, 0.2 percent copper, and 2.0 percent platinum; and
a power supply, said power supply in electrical communication with said electrode and with an electrode pad on the patient.

15. An apparatus comprising:
(A) an electrically insulative member having a first lumen, a proximal end and a distal end;
(B) an electrical conductor extending through said first lumen;
(C) a first electrode extending out of said distal end for the in situ creation and release of cations from the said first electrode directly into the blood from the circulatory system of a patient, said first electrode defining a distal end configured and dimensioned for passage through the patient's skin and into the blood of the patient's venous system, said first electrode being solid and in electrical communication with said electrical conductor; said first electrode is comprised of approximately 97.8 percent silver, 0.2 percent copper, and 2.0 percent platinum; and
(D) a power supply, said power supply in electrical communication with said first electrode and with a second electrode, said second electrode being in electrical communication with said first electrode via the patient's blood.

16. An apparatus comprising:
(A) a catheter having a proximal end and a distal end;
(B) an electrical conductor extending through said catheter;
(C) a first electrode extending out of said distal end of said catheter for the in situ creation and release of cations from the electrode directly into the blood from the circulatory system of a patient, said first electrode defining a distal end configured and dimensioned for passage through the patient's skin and into the blood of the patient's venous system, said first electrode being in electrical communication with said electrical conductor; said first electrode is comprised of approximately 97.8 percent silver, 0.2 percent copper, 2.0 percent platinum; and
(D) a power supply, said power supply in electrical communication with said first electrode and with a second electrode, said second electrode being in electrical communication with said first electrode via the patient's blood.

17. A method for the destruction of blood borne pathogens comprising:
(A) inserting a first metal electrode into a patient's blood, said the first metal electrode comprising silver;
(B) placing a second electrode in electrical communication with the first metal electrode via the patient's blood;
(C) applying a first low intensity direct current to the first metal electrode for a first period of time; said first low intensity direct current is approximately two and one-half microamps; and (D) applying a second low intensity direct current to the first metal electrode for a second period of time; said second low intensity direct current is approximately one hundred and twenty-five nanoamps.

18. The method of claim 17 wherein said first period of time is approximately twelve minutes and said second period of time is approximately seventy-one hours and forty-eight minutes.

19. The method of claim 17 wherein said first period of time is approximately twelve minutes and said second period of time is approximately six weeks.

20. Apparatus for the destruction of a blood borne viral pathogen comprising:
(A) a first electrode for the in situ creation and release of cations from the electrode directly into the blood of a patient's venous system, the first electrode being at least partially disposed in a catheter lumen and having an exposed portion extending out of the distal end of the catheter lumen and a non-exposed portion disposed within the catheter lumen;
(B) a second electrode for placement on a patient's skin;
(C) conductive means for electrically connecting the first and second electrodes to power supply means; and
(D) power supply means for applying low-intensity direct current to the first electrode in a pattern sufficient to destroy the blood borne viral pathogen through the release of pathogen-binding cations from the first electrode into the blood of the venous system of the patient.

21. The apparatus of claim 20 wherein the first electrode includes an electrical conductor portion disposed within the catheter lumen and an electrode portion extending out of the distal end of the catheter lumen for the in situ creation and release of cations directly from the electrode directly into the blood of the venous system of a patient, the electrode portion being in electrical communication with the electrical conductor portion and releasing pathogen-binding silver cations.

22. Apparatus for the destruction of a blood borne viral pathogen comprising:
(A) a first electrode for the in situ creation and release of cations from the electrode directly into the blood from a patient's venous system, said first electrode being at least partially disposed in a catheter lumen and having an exposed portion extending out of the distal end of the catheter lumen and a non-exposed portion disposed within the catheter lumen;
(B) a second electrode, said second electrode being in electrical communication with said first electrode via the patient's blood;
(C) conductive means for electrically connecting said first and second electrodes to power supply means; and
(D) power supply means for applying low-intensity direct current to said first electrode in a pattern sufficient to destroy the blood borne viral pathogen through the release of pathogen-binding cations from said first electrode into the blood from the circulatory system of the patient.

23. The apparatus of claim 22 wherein said first electrode includes an electrical conductor portion disposed within the catheter lumen and an electrode portion extending out of the distal end of the catheter lumen for the in situ creation and release of cations from the electrode directly into the blood from the circulatory system of a patient, said electrode portion being in electrical communication with said electrical conductor portion and releasing pathogen-binding silver cations.

* * * * *